United States Patent [19]

Oliver et al.

[11] Patent Number: 4,848,141

[45] Date of Patent: Jul. 18, 1989

[54] METHOD FOR CONTINUOUS DETERMINATION OF THE ELASTIC STIFFNESS OF CONTACT BETWEEN TWO BODIES

[76] Inventors: Warren C. Oliver, 925 Forest Ridge Circle, Knoxville, Tenn. 37932; John B. Pethica, 34 Feilden Grove, Oxford, England, OX 3-ODU

[21] Appl. No.: 178,397

[22] Filed: Apr. 6, 1988

[51] Int. Cl.⁴ .......................................... G01N 3/42
[52] U.S. Cl. ....................................................... 73/81
[58] Field of Search ............................... 73/78, 81, 573

[56] References Cited

U.S. PATENT DOCUMENTS 3,958,450  5/1976  Kleesattel .............................. 73/573

Primary Examiner—Stewart J. Levy
Assistant Examiner—Lawrence G. Fess

[57] ABSTRACT

A method for continuously measuring the stiffness and area of contact between two bodies is provided. Elastic stiffness of a junction is measured by introducing a relatively small oscillatory mechanical force at a known frequency to the junction and measuring the subsequent displacement response using AC signal-handling techniques to provide a continuous measurement proportional to the stiffness and the area of contact between the bodies, even as the area of contact changes.

15 Claims, 5 Drawing Sheets

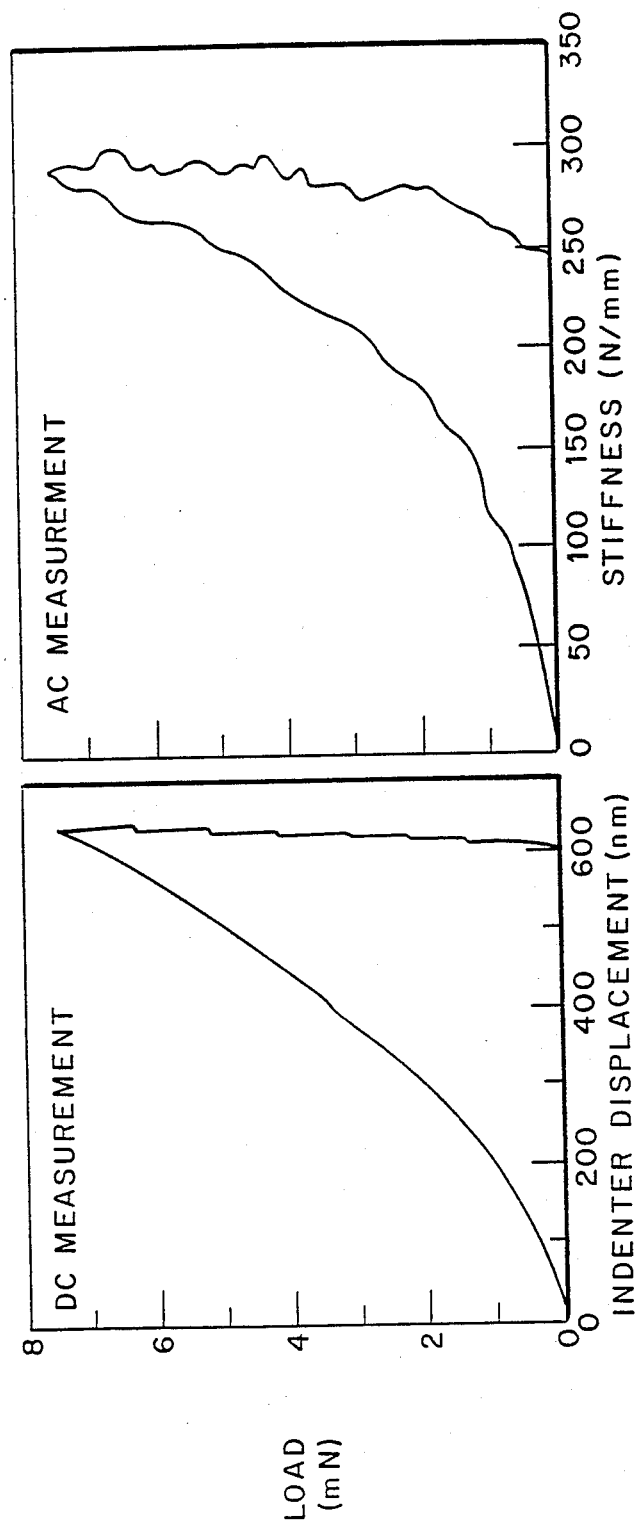

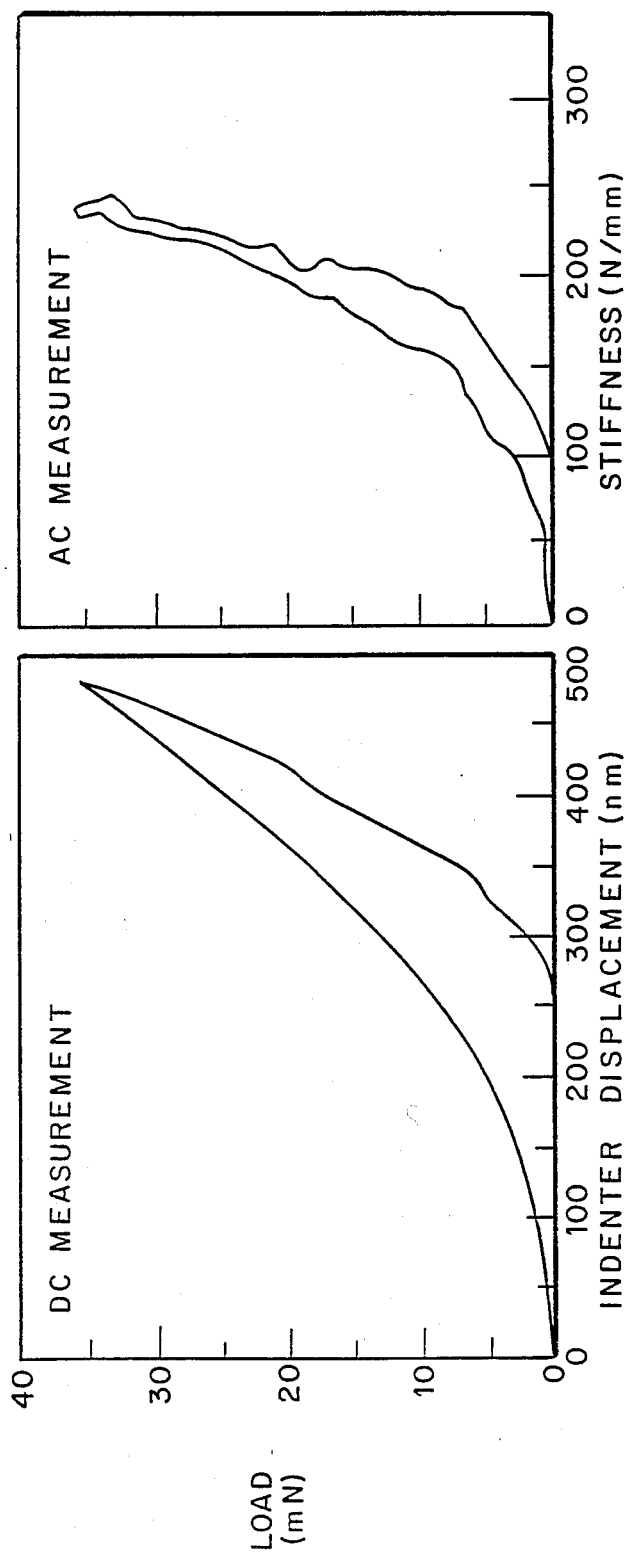

METHOD FOR CONTINUOUS DETERMINATION OF THE ELASTIC STIFFNESS OF CONTACT BETWEEN TWO BODIES

BACKGROUND OF THE INVENTION

This invention, which is a result of a contract with the U.S. Department of Energy, relates generally to methods and systems for measuring mechanical properties of materials, and more specifically to improvements in microindentation methods for measuring mechanical properties of materials.

There are numerous applications in which a dynamic measure of the stiffness and contact area between two bodies is an important factor. For example, a mechanical properties microprobe can provide a wide range of material properties from a simple microindentation test if properly instrumented. The measurements of yield strength, creep resistance, stress relaxation, modulus, fracture toughness and even fatigue are possible. Other applications in which a dynamic measure of contact area is necessary include electronic characterization of materials using point probes such as in the semiconductor industry, micromachining techniques for use in making controlled submicron scratches to produce lithographic masks, thin film properties and thickness measurement, and surface coating quality control.

The contact area between two bodies is difficult to determine when the area of contact is less than a few square microns. Prior art techniques for obtaining such measurements include measuring the physical interference (depth of contact) between the bodies and measuring the electrical resistance at the junction. In another method, the contact area between sample and indenter may be measured optically after the indenter is removed and the assumption is made that the area does not change on unloading. Each of these methods have several drawbacks that limit their usefulness.

Although imaging indents does give a direct measure of the area of contact, it becomes more difficult as the size of the indent is reduced. Submicron sized indents can only be imaged using electron microscopy. The techniques used are time consuming and only yield the final size of the indent.

One geometric characteristic of the indent that is more easily measured and can be measured continuously during the entire indentation process is the displacement of the indenter after contact. This measurement provides several other distinct advantages over direct area measurement. These include the ability to sample both elastic and plastic strains, the ability to both control and monitor stress and strain rates, and finally the elimination of the need for complicated, time consuming imaging techniques. The displacement can be measured with sufficient resolution to characterize extremely small indents; however, mathematical models of the indentation process must be employed to allow the contact area to be calculated. These models have been developed and used successfully. Further details of the models and their successful use may be found in the following references, the subject matter of which is included herein by reference thereto.

1. W. C. Oliver, R. Hutchings, and J. B. Pethica, "Measurements of Hardness at Indentation Depths as Low as 20 Nanometers"; pp 90-108 in ASTM Special Technical Publication No. 889, 1986.

2. S. I. Bulychev, V. P. Alekhin, M. K. H. Shorshorov, A. P. Ternovskii and G. D. Shnyrev, Zayod. Labor., 41(9) (1975).

An ultra low force indentation system sold under the trade name Nanoindenter is commercially available from Microsciences, Inc., Norwell, MA 02061. This system, modified according to the present invention, is shown schematically in FIG. 1. In this system, measured force is applied to the indenter electromagnetically and can be ramped up and down linearly over a range of rates. The area of the indentation is determined as a function of displacement of the indenter by measuring the displacement of the indenter after contact with the sample by means of a capacitive displacement gage. The area of the contact is a critical parameter, especially as the indented area becomes smaller and smaller, e.g., <a few microns$^2$.

Further information can be obtained from an indentation test consisting of a series of loading and unloading sequences going to progressively higher maximum loads. Thus, by loading and unloading the indenter, a plot of load versus indenter displacement is obtained which permits determination of both plastic (permanent) and elastic (resilient) deformation properties for the material being tested. Displacement measurements made during loading sequences in which the size of the indent is increased plastically, contain information about both the elastic and plastic strain fields. The unloading data represents the response of the elastic field only. Using information from both sequences of data, the plastic and elastic components can be separated; hence, the contact area, the hardness, and the modulus can be calculated, using the mathematical models for the material, for each point at which an unloading sequence begins using the relationships set forth below in equations (1) through (4).

The contact stiffness $S=dP/dh_T$ for two bodies in contact under load P, $h_T$ being the displacement of the indenter body beyond the point of contact, is measured directly at each unloading point which is the slope of the unloading curve at that point. This stiffness measurement along with the measured load, or contact force, P and the displacement $h_T$ is used to determine the various mechanical properties of a sample under test in accordance with the following relationships:

$$h_I = h_T - \epsilon(P/S) \qquad (1)$$

where:
 $h_I$ = the plastic depth of the indent, or contact area depth (see FIGS. 3 and 4); and
 $\epsilon$ = an experimentally determined constant related to the indenter geometry.

Knowing $h_I$, the area of contact (A) is determined as a function of $h_I$ as follows:

$$A = f(h_I). \qquad (2)$$

Once the area of contact A has been determined, the hardness (H) of the sample may be determined from the following relation ship:

$$H = P/A \qquad (3)$$

where:
 P = the applied DC load.

Once the above parameters are known, the modulus of the sample may be determined from the following relationship:

$$S \approx (2/\sqrt{\pi})\sqrt{A}(E_r) \qquad (4)$$

where:

$E_r$ = Composite modulus of indenter and specimen, i.e., $$E_r = \left[ \frac{1 - \gamma_s^2}{E_s} + \frac{1 - \gamma_I^2}{E_I} \right]^{-1}$$

where:

$E_I$ = Modulus of Indenter;
$\gamma_I$ = Poison's Ratio of Indenter;
$E_s$ = Modulus of Sample; and
$\gamma_s$ = Poison's Ratio of Sample.

While the above sequence of measurements can yield important information on various mechanical properties of materials, repeated loading and unloading sequences cause problems with some materials due to the effects of changes in the strain rate on the properties measured, since the loading sequence must be interrupted to make the stiffness measurements. Thus, there is a need for an improved method of measuring the elastic stiffness of contact between two bodies which allows continuous measurement of stiffness. Further, there is a need for a method to not only continuously measure the stiffness of a contact between two bodies, but also continuously provide the true contact area between the two bodies.

SUMMARY OF THE INVENTION

In view of the above need, it is an object of this invention to provide a method for continuously measuring the stiffness of contact between two bodies.

Another object of this invention is to provide a method for detecting the point of contact between two bodies.

Yet another object of this invention is to provide a method for direct, continuous measure of the contact area between two bodies as plastic deformation occurs there between.

Other objects and many of the attendant advantages of the present invention will become apparent to those skilled in the art from the following detailed description taken in conjunction with the drawings.

Briefly, the invention is a method for continuously measuring the stiffness of contact between first and second bodies, comprising the steps of: applying an oscillatory mechanical force of a known magnitude to the mechanical contact junction of the bodies; and, simultaneously measuring the phase and amplitude of the resulting oscillatory displacement between the bodies relative to the applied oscillatory force as an indication of the stiffness of contact between the bodies.

A further aspect of this invention is to provide a method for continuously measuring the stiffness of contact between first and second bodies even though the contact area between the two bodies is changing and to further continuously determine the contact area between the bodies.

In accordance with a further aspect of this invention a method is provided for continuously measuring the elastic response of a mechanical junction between an indenter and a sample material by applying a predetermined increasing direct force to said indenter to load the junction while applying a relatively small amplitude oscillatory force to the junction of sufficient magnitude to alternately load and unload the junction while continuously measuring both the amplitude and phase of the resulting displacement of the indenter relative to the applied oscillatory force as a continuous indication of the stiffness of the junction as the indenter is forced against the sample in a process of measuring various other mechanical properties of the sample material.

In accordance with a further feature of this invention, a method is provided to measure stiffness (i.e., elastic and inelastic response) of a sample material in an indentation test system, wherein an indenter probe is forced into contact with the sample over a loading and unloading cycle, as the indentation process is carried out without interrupting the continuity of the process. This is made possible by superimposing a relatively high frequency AC signal source onto a DC signal used to drive a force generating means that applies the force to the indenter probe. The DC driving force is a very slow changing applied force. The AC driving force is sized such that a displacement amplitude (typically 10 Angstroms prior to contact) results. The force alternates at a selected frequency which can range from about 0.5 Hz to 1 MHz (megahertz) depending on the mechanics of the indenter probe assembly and the capabilities of the detection electronics. The alternating displacement component of the signal taken from a displacement gage is monitored by a frequency specific amplifier which also determines the phase of the signal relative to the applied AC drive signal. This provides a measure of the slope of the unloading versus displacement curve, i.e., continuous measurement of the elastic load/displacement response of the contact of the indenter with the sample. This approach yields the desired measurement of stiffness without significantly changing the DC force component acting on the junction.

Using this method, a direct, virtually instantaneous and continuous measure of stiffness of the contact junction between the indenter and the sample is obtained as a function of the oscillatory displacement of the indenter probe tip during the process of loading and unloading the indenter and sample junction, i.e., as plastic deformation of the sample occurs.

BRIEF DESCRIPTION OF THE DRAWINGS

FIG. 5 is a graph illustrating the effect of applied load on indenter probe tip displacement (FIG. 5a) and on surface stiffness (FIG. 5b) for a diamond tip contacting a sample of electropolished, annealed copper.

FIG. 7 is a graph illustrating the effect of applied load on indenter probe tip displacement (FIG. 7a) and on surface stiffness (FIG. 7b) for a diamond tip contacting a sample of silicon with a 25 nanometer (nm) plastic film disposed thereon.

DETAILED DESCRIPTION

Figure 1:
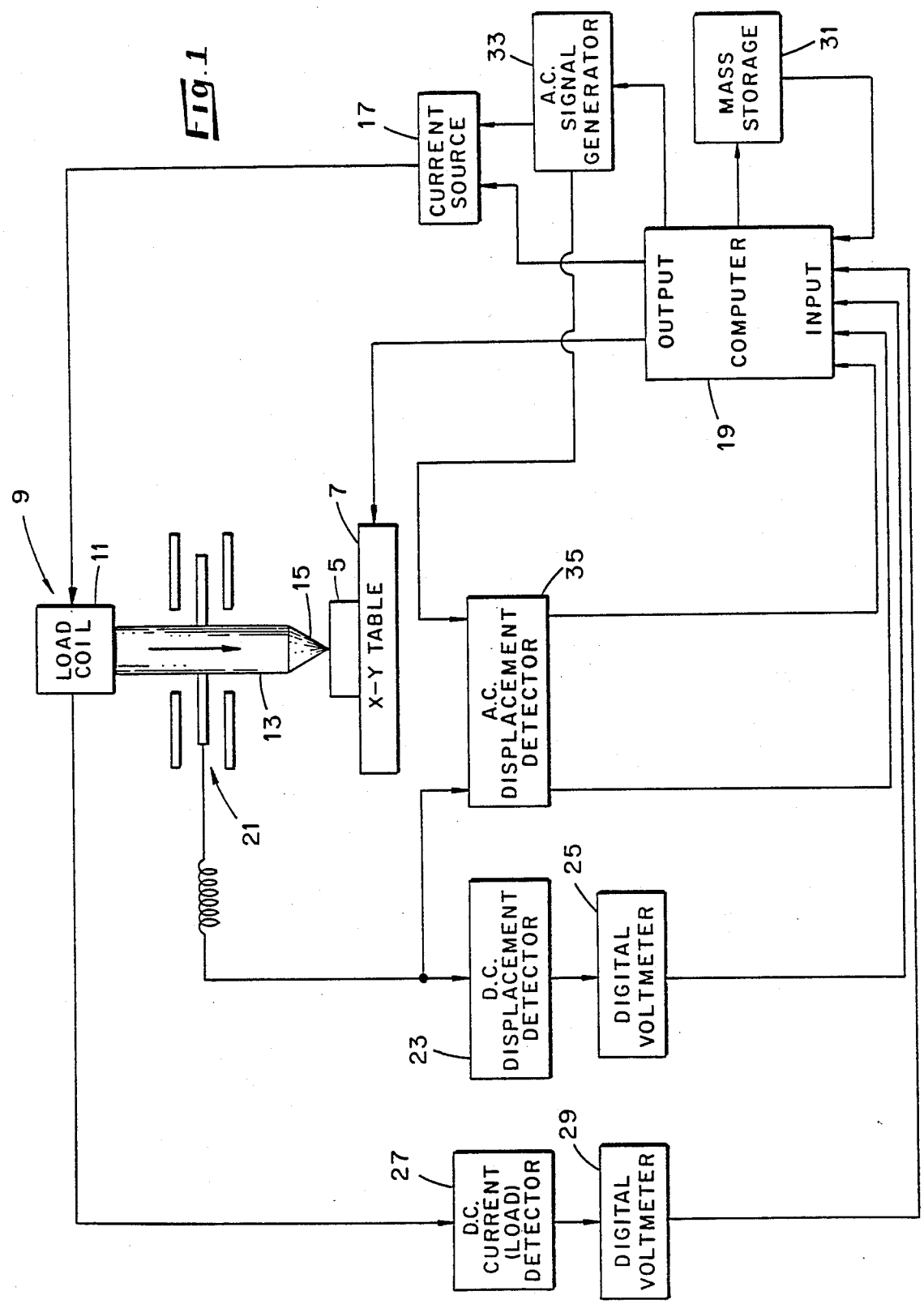
FIG. 1 is a schematic diagram of a commercially available indentation testing system modified to carry out the method of continuously measuring the stiffness of contact between an indenter probe and a sample in accordance with the present invention.

Referring now to FIG. 1, there is shown a schematic diagram of an indentation system, such as the Nanoindenter system referenced above, modified in accordance with the present invention for testing a sample of material 5. The sample 5 is placed at a known location on a computer controlled X-Y table 7 with the surface to be tested facing up. An electromagnetically driven indenter arrangement 9 is provided which is positioned over the sample 5. The indenter 9 includes a current driven load coil 11 activated by the application of electrical current from a computer controlled variable current source 17 to move the probe tip 15 downward into engagement with the sample 5. Once the tip contacts the sample a preselected force pattern is applied to the indenter by the programmed variation of the current applied to the drive coil 11. The probe tip 15 may be in the form of a typical triangular pyramidal diamond probe with an end radius of about 500 Angstroms.

The current source 17 is controlled by the system computer 19 which also controls the X-Y table 7. The displacement of the probe 13 is measured by a capacitive displacement gage 21, whose output is connected to a DC displacement detector 23. The detector 23 digitizes the DC displacement signal which is fed through a digital voltmeter 25 to an input of the computer 19. The voltmeter 25 provides a calibrated readout of the probe displacement to an operator during testing procedures.

The force applied to the sample through the indenter probe 13 is monitored by a DC current detector 27 which senses the DC drive current applied to the load coil 11. The DC load current is digitized by the detector 27 and fed through a second digital voltmeter 29 to a further input of computer 19. The computer may be connected to a mass storage device 31 in which data and system operating parameters are stored.

Using the system as described above, a sample 5 is positioned at a known location on the X-Y table 7 and the programed computer 19 is signaled to start the test procedure. The computer is programed to perform a prescribed indentation test, single or multiple indentations at designated locations on the sample, automatically. The probe is lowered at a very slow rate until contact is made with the sample. Then the computer applies a programmed increasing DC current from source 17 to the load coil 11 of the indenter which forces the indenter against the sample 5 until a preselected junction loading or displacement level is reached and then the force is removed at the same rate to unload the junction. During this loading and unloading cycle, the computer records the junction loading taken from the DC current (load) detector 27 and the probe displacement taken from the DC displacement detector 23. These values may be stored in the mass storage unit 31 for subsequent use in determining the various mechanical properties of the sample as outlined above.

In accordance with the method of this invention, to continuously measure the stiffness of the contact between two bodies such as the indenter probe tip 15 and the sample 5 during the loading and unloading cycle, the above Nanoindenter system is modified to include a means for applying a small mechanical vibrational force to the junction of the indenter probe and the sample and monitoring the resulting displacement relative to the applied force as a measure of the stiffness between the two bodies. The force may be applied in the form of an oscillatory force (AC force), typically about $10^{-8}$ N (Newton), by superimposing an AC current onto the DC drive current applied to the drive coil 11. The frequency of the AC force applied is typically in the range of from 0.5 to 200 Hz for the system depicted in FIG. 1; however, depending on the design of the probe mounting assembly involved, the concept can work from about 0.5 Hz to 1 MHz. The amplitude of the oscillating force may be in the range of from about $10^{-10}$ to 1 N, depending on the area of the contact.

This procedure may be accomplished by adding an AC signal generator 33 under control of the computer 19 to inject an AC signal into the output current signal of the current source 17 and detecting the resulting AC displacement by means of an AC displacement detector 35. The detector 35 may be a lock-in amplifier which is tuned to measure the amplitude of the AC displacement at the applied frequency together with the phase of the displacement signal relative to the applied signal. The amplitude and phase signals are digitized by the detector 35 and fed to separate inputs of the computer 19 for analysis or storage along with the DC force and displacement information during a loading and unloading cycle.

Using the AC force (F), phase ($\phi$) and AC displacement $h(\omega)$ information, the stiffness (S) may be determined continuously in accordance with the following relationship:

$$\tan(\phi) \simeq \frac{\omega c}{S + k - m\omega^2} \quad (5)$$

where:
  $\omega$ = frequency of applied AC force component;
  c = damping coefficient of the probe mounting assembly;
  k = probe mounting assembly spring constant; and,
  m = probe and assembly mass.

Figure 2:
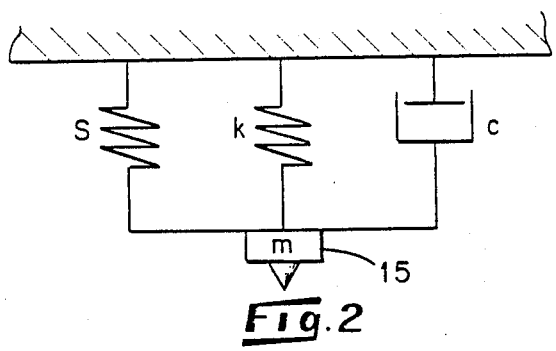
FIG. 2 is a schematic illustration of the dynamic components of the indenter probe mounting assembly including the mass m, mounting spring constant k, damping coefficient c and tip-surface interaction stiffness S.

The dynamic elements of the probe mounting assembly are illustrated schematically in FIG. 2. The probe assembly of the Nanoindenter system is supported by leaf springs (not shown) which constrain it to move only in a direction normal to the sample 5 surface. As the probe tip 15 approaches the sample surface to be tested, the stiffness S appears as a spring in parallel with the probe assembly mounting springs. Thus, the stiffness may be calculated by the computer using equation 5 or could be displayed on a separate voltmeter (not shown) connected to the phase signal output of detector 35 and calibrated in accordance with equation 5. It will be seen that the value of S as the probe tip 15 approaches the sample will remain constant until contact with the sample surface is made. This sudden change in S may be used to indicate the point of contact with the surface.

The above approach to the measurement of stiffness is the most sensitive at low stiffness values, less than about $10^4$ N/m. Alternatively, the stiffness may also be determined from the ratio of the AC signal modulation force (F) to the corresponding AC displacement [h(ω)] in accordance with the following relationship:

$$\left|\frac{F}{h(\omega)}\right| \simeq \sqrt{(S + k - m\omega^2)^2 + \omega^2 c^2} \quad (6)$$

Thus, it will be seen that signals proportional to both values of S are available from the outputs of the detector 35 which measures the amplitude and phase of the AC displacement force.

Equations 5 and 6 will change if an alternative dynamic model is necessary to describe the particular loading system used to perform the tests. In addition it is possible to use an oscillatory displacement excitation and measuring the resulting oscillatory force signal. In this case, the same equations and techniques are used to determine the stiffness of the contact. The design of such models (as shown in FIG. 2) and the equations that are used to represent their dynamic response are well known in the art.

Figure 3:
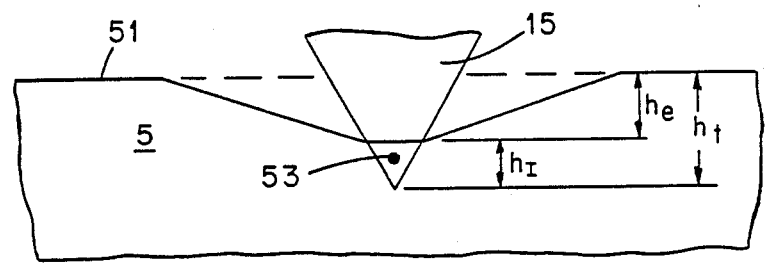
FIG. 3 is a schematic illustration of a typical deformation pattern of a sample as an indenter probe tip is forced into contact with the sample.
Figure 4:
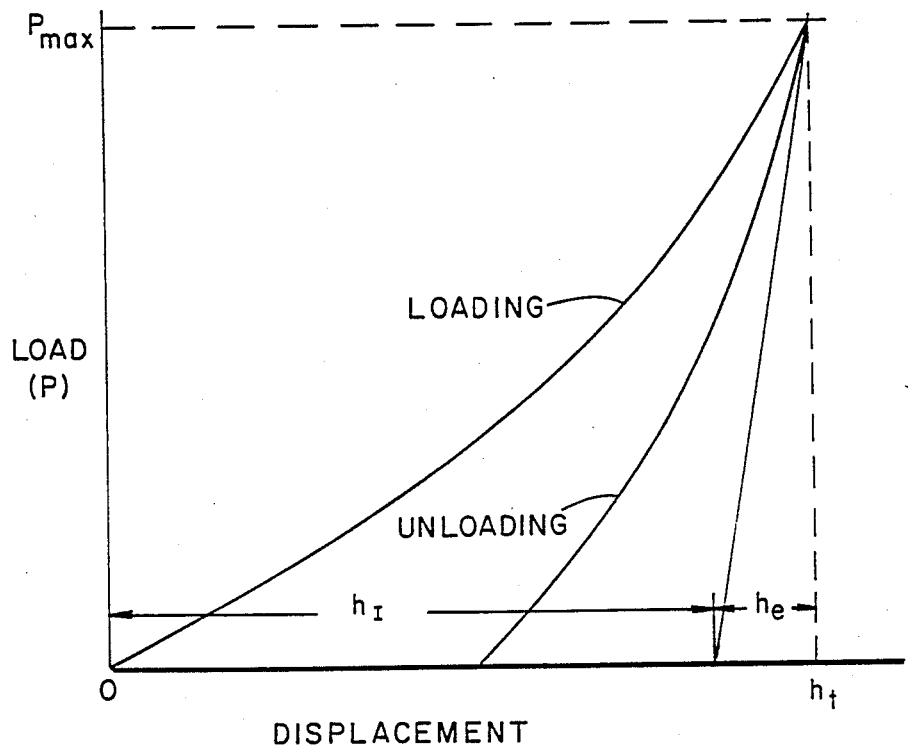
FIG. 4 is a graph illustrating a typical indentation test loading and unloading curves of load versus displacement and further illustrates the method of determining the contact area between the indenter probe tip and the sample.

Referring now to FIGS. 3 and 4, it will be illustrated how the probe tip contact area A is determined from the information obtained using this method. As shown in FIG. 3, when the indenter probe tip 15 contacts the sample 5 surface 51, the surface will yield over a greater area than that which is in contact with the probe tip 15 which is indicated by the actual contact area 53. It is this actual contact area (A) which must be measured to provide accurate calculations based on the contact area. With reference to the graph of FIG. 4, which illustrates typical loading and unloading curves for an indenter test cycle of a material such as copper for example which is loaded to a value of $P_{max}$ prior to unloading, the manner in which the contact area is determined will be described. Since the stiffness of the sample $S = dP/dh_T$ at $P_{max}$ is the slope of the unloading curve at $P_{max}$, as illustrated by the straight line drawn from $P_{max}$ to the displacement axis, it follows that $h_e \simeq \epsilon(-P_{max}/S)$, where $\epsilon$ is a constant related to the geometry of the indenter tip, $h_T$ is the total displacement and $h_e$ is the noncontacting portion of the tip displacement. For a flat punch tip surface, $\epsilon = 1$ and for a conical type tip $\epsilon = 0.68$. This constant, for the specific indenter geometry used, is determined experimentally using standard materials of known modulus. Thus, measuring the total displacement ($h_T$), $P_{max}$ and S (stiffness) $h_e$ may be determined. Knowing $h_T$ and $h_e$, the indenter contact depth $h_I$ may be calculated as $h_I = h_T - h_e$; and, thus the contact area A may be determined as a function of $h_I$ using equation 1, i.e., $A \simeq f(h_I)$. For example, $A = 24.5 \cdot (h_I)^2$ for a perfect three sided pyramid with an angle of 65° between its central axis and one face. For the indenter used in the examples shown in FIGS. 5 through 7, the area function was experimentally determined to be $A = 24.56(h_I)^2 + 225.9(h_I)^{3/2} + 519.6(h_I)$, where $h_I$ is in nanometers and A is in (nanometers)$^2$.

Once the contact area is determined, the hardness and modulus of the test sample may be determined using the area value in equations (3) and (4), respectively.

In applications where the modulus of the indenter and sample are known and remain constant, the area of contact A may be determined directly using equation 4 by substituting a constant $k_E$ for $E_r$ and solving for A as follows:

$$A \simeq 2/\pi^2 (S/k_E)^2.$$

Therefore, it will be seen that the AC signal imposed on the DC driving force signal for the probe provides, in effect, continuous load/unload cycles which provide a continuous load/displacement response of the contact between the indenter probe and the sample which is directly related to the stiffness of contact between the bodies. Using this technique, a direct, virtually instantaneous and continuous measure of the stiffness and area of contact between the indenter and the sample as the junction is made, i.e., as plastic deformation occurs. This technique may be used not only in microprobe testing of materials, but may be used to control a cutting tool in micromachining applications by maintaining a constant contact area between the cutting tool and the work piece using the method of this invention.

The following example illustrates how the present microindentation technique can yield a continuous measure of the stiffness and thus the area of contact between a diamond indenter probe tip and various sample materials in a microindentation process for purposes of measuring mechanical properties of the samples.

EXAMPLE

Using the Nanoindenter system as referenced above and modified as shown in FIG. 1, a series of microindentations were made in the surface of copper, sapphire, and silicon with a thin plastic overlay. The data required were obtained by monitoring the AC signal superimposed on the DC driving signal to provide a multiplicity of loading and unloading sequences over a complete indentation cycle. Two sets of data were obtained for each test, one representing the pure DC measurement and the other representing the AC monitoring signal in accordance with this invention. In each test, the AC signal frequency was 69.3 Hz and the AC driving current was 0.06 amps resulting in an oscillatory force of 0.12 N. From these tests, load versus displacement and load versus stiffness curves were plotted to yield information about the plastic and elastic strain fields of the samples. Results are illustrated in FIGS. 5 through 7.

FIG. 5a shows the indenter displacement versus load as obtained by the prior DC force measuring method while FIG. 5b shows the stiffness versus load result using the subject invention for an electropolished, annealed copper sample. A large load was used in this test resulting in a large displacement for which the prior DC measurement method is adequate. Note that the output obtained by the subject invention, FIG. 5b, is similar in shape and is effective up to a few microns indent depth. With this sample the amplitude method of stiffness calculation (equation 6) was used.

Figure 6B:
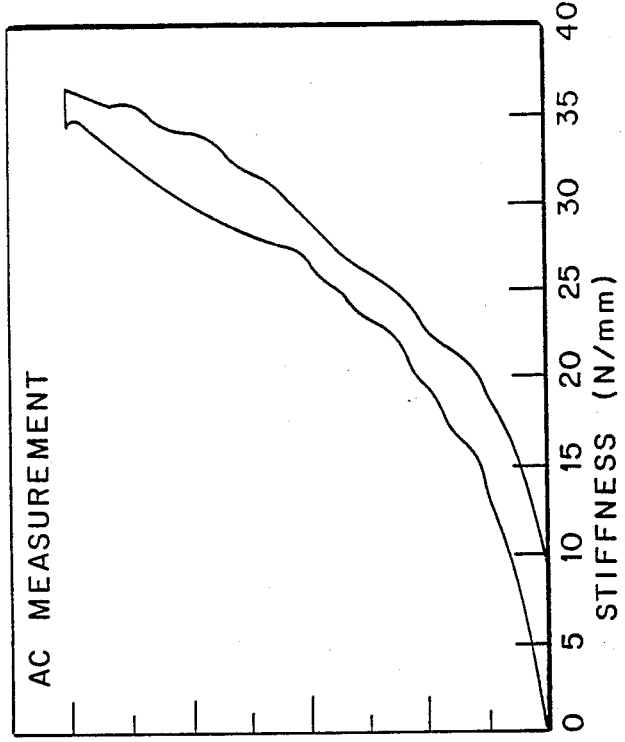
FIG. 6 is a graph illustrating the effect of applied load on indenter probe tip displacement (FIG. 6a) and on surface stiffness (FIG. 6b) for a diamond tip contacting a sample of sapphire along the C-axis.
Figure 6A:
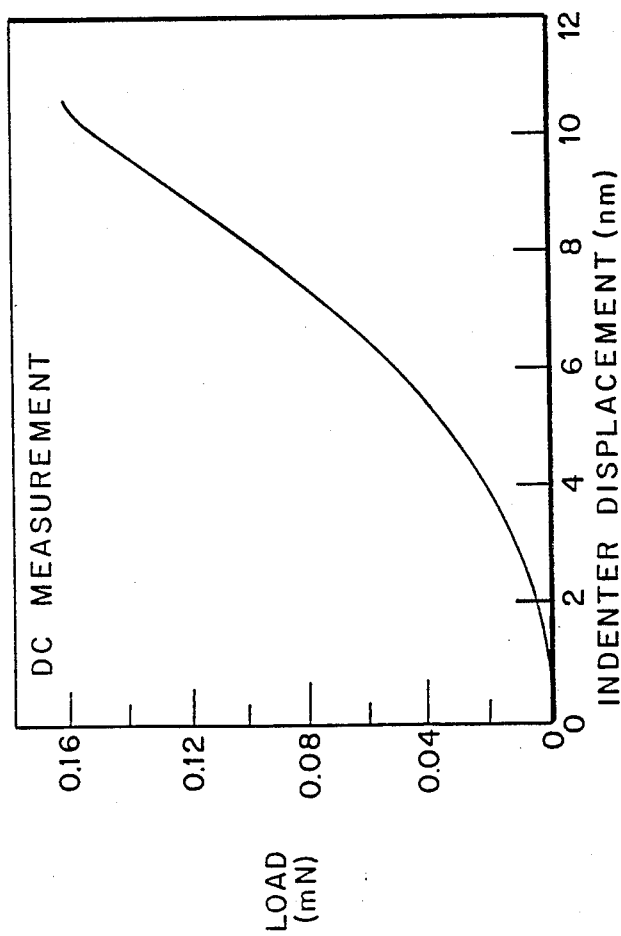

FIG. 6 shows the results of a low load test on sapphire showing reversible contact. Thermal drift in the DC displacement measurement was very small in this run. The subject technique also shows reversibility and does so more consistently. The AC phase detection method of equation 5 was used in this test to determine the stiffness.

FIG. 7 shows the results of measurements on silicon having a thin plastic film coating. The DC method for measuring contact area is difficult to use, particularly where there are large differences in properties of the film and substrate. Plastic strain fields in such cases are very inhomogeneous. FIG. 7b shows that the subject invention samples elastic strain fields which tend to be more homogeneous. The AC amplitude method was used to determine the stiffness in this sample.

This invention has distinct advantages over other methods for measuring physical parameters of materials. These advantages include applicability to any material (regardless of its electrical properties), extreme sensitivity at very small contact areas, insensitivity to thermal drift of the displacement sensing instrument, and ease of measurements.

Further, the principles involved in making the above measurements may be expanded to other technical problems in which contact area between two bodies is a process controlling parameter. Possible applications include thin film characterization, micromachining, microscribing, controlling the contact process between a point and a surface, electrical measurements involving pointed probes in which the contact area is an important consideration, detecting the point of initial contact between two bodies and possibly even measuring interatomic potentials.

Thus, it will be seen that a very versatile method has been provided for continuously measuring the stiffness of contact between two bodies even though the contact area is changing and further determine the true contact area between the two bodies. Although the invention has been illustrated by means of its application to a microindentation testing system, it will be apparent to those skilled in the art that the method may be applied in various aspects, with various modifications and changes, without departing from the spirit and scope of the invention as set forth the following claims which form a part of this specification.

We claim:

1. A method for continuously measuring the stiffness of contact between first and second bodies, comprising the steps of:
    applying an oscillating mechanical excitation at an arbitrary selected fixed frequency and a known amplitude to the contact junction of said first and second bodies; and, simultaneously applying a load independently of said fixed frequency to the contact junction;
    measuring the resulting mechanical response between said first and second bodies relative to the applied oscillatory excitation at said load as an indication of the stiffness of contact between said first and second bodies.

2. A method for continuously measuring the stiffness of contact between first and second bodies, comprising the steps of:
    applying an oscillating mechanical force (F) at an arbitrary selected fixed frequency and a known amplitude to the contact junction of said first and second bodies; and, simultaneously applying a load independently of said fixed frequency to the contact junction;
    measuring the resulting oscillatory displacement response between said first and second bodies relative to the applied oscillatory force at said load as an indication of the stiffness of contact between said first and second bodies.

3. The method as set forth in claim 2 further including the simultaneous step of introducing a controlled, direct mechanical force to said contact junction of said first and second bodies which is applied over a loading and subsequent unloading cycle to vary the junction loading.

4. The method as set forth in claim 3 wherein said measuring step includes measuring the phase $\phi$ and amplitude $h(\omega)$ of the resulting oscillatory displacement between said first and second bodies as an indication of the stiffness of contact between said first and second bodies.

5. The method as set forth in claim 4 wherein said second body is a sample material and said first body includes an indenter probe assembly having a probe tip mounted to be controllably forced into contact with said sample material and means for applying said direct and oscillatory forces to said junction between said bodies.

6. The method as set forth in claim 5 wherein said measuring step further includes the step of determining the stiffness (S) of contact between said first and second bodies in accordance with the relationship:

$$\tan(\phi) \simeq \frac{\omega c}{S + k - m\omega^2};$$

where $\omega$ is the frequency of said oscillatory force, K is the spring constant of said probe assembly, c is the damping coefficient of said probe assembly, and m is the mass of said probe assembly.

7. The method as set forth in claim 5 wherein said measuring step includes determining the stiffness (S) of contact between said first and second bodies in accordance with the relationship:

$$\left|\frac{F}{h(\omega)}\right| \simeq \sqrt{(S + k - m\omega^2)^2 + \omega^2 c^2};$$

where $\omega$ is the frequency of said oscillatory force, k is the spring constant of said probe assembly, c is the damping coefficient of said probe assembly, and m is the mass of said probe assembly.

8. The method as set forth in claim 6 further including the steps of determining the plastic indentation depth ($h_I$) of said probe tip into said sample material in accordance with the relationship:

$$h_I = h_T - \omega(P/S);$$

where $h_T$ is the total indentation depth of said probe tip into said sample material beyond the point of contact with said sample material; and determining the area of contact (A) of said indenter probe tip with said sample material in accordance with the relationship:

$$A \simeq f(h_I).$$

9. The method of claim 8 further including the step of determining the hardness (H) of said sample material in accordance with the relationship:

$$H = P/A.$$

10. The method of claim 9 further including the step of determining the modulus ($E_s$) of said sample material in accordance with the relationship:

$$S \simeq (2/\sqrt{\pi})\sqrt{A}(E_r);$$

where $E_r$ is the composite modulus of said probe tip and said sample material which is defined as follows:

$$E_r = \left[ \frac{1-\gamma_s^2}{E_s} + \frac{1-\gamma_I^2}{E_I} \right]^{-1};$$

where $E_I$ is the modulus of said probe tip, $\gamma_I =$ Poison's Ratio of said probe tip, and $\gamma_s =$ Poison's Ratio of said sample material.

11. The method as set forth in claim 7 further including the steps of determining the plastic indentation depth ($h_I$) of said probe tip into said sample material in accordance with the relationship:

$$h_I = h_T - \omega(P/S);$$

where $h_T$ is the total indentation depth of said probe tip into said sample material beyond the point of contact with said sample material; and determining the area of contact (A) of said indenter probe tip with said sample material in accordance with the relationship:

$$A \simeq f(h_I).$$

12. The method of claim 11 further including the step of determining the hardness (H) of said sample material in accordance with the relationship:

$$H = P/A.$$

13. The method of claim 12 further including the step of determining the modulus ($E_s$) of said sample material in accordance with the relationship:

$$S \simeq (2/\sqrt{\pi})\sqrt{A}(E_r);$$

where $E_r$ is the composite modulus of said probe tip and said sample material which is defined as follows:

$$E_r = \left[ \frac{1-\gamma_s^2}{E_s} + \frac{1-\gamma_I^2}{E_I} \right]^{-1}$$

where $E_I$ is the modulus of said probe tip, $\gamma_I =$ Poison's Ratio of said probe tip, and $\gamma_s =$ Poison's Ratio of said sample material.

14. The method as set forth in claim 5 wherein the modulus of said first and second bodies is known and further including the step of determining the area (A) of contact between said first and second bodies in accordance with the relationship:

$$A \simeq 2/\pi^2 (S/k_E)^2;$$

where S is the stiffness of contact between said first and second bodies and $k_E$ is a constant whose value depends on the known composite modulus of said first and second bodies.

15. A method for continuously measuring the stiffness of contact between an indenter probe and a sample being tested in an indentation testing system including a computer for controlling the application of a direct mechanical force to the junction between said probe and said sample and monitoring the displacement of said probe so as to determine mechanical properties of said sample as said direct mechanical force is applied in accordance with a selected loading and subsequent unloading cycle of said junction, comprising the steps of:

applying an oscillatory mechanical force to said junction superimposed on said direct mechanical force of sufficient frequency and amplitude to continuously load and unload said junction, and simultaneously measuring the resulting oscillatory displacement response of said probe relative to the applied oscillatory mechanical force as an indication of the stiffness of contact between said probe and said sample.

* * * * *